(12) United States Patent
Penn et al.

(10) Patent No.: US 9,739,791 B2
(45) Date of Patent: Aug. 22, 2017

(54) METHODS FOR PREDICTING AND TREATING MYOCARDIAL DAMAGE

(71) Applicant: THE CLEVELAND CLINIC FOUNDATION, Cleveland, OH (US)

(72) Inventors: Marc S. Penn, Beachwood, OH (US); Edward J. Lesnefsky, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 15/429,766

(22) Filed: Feb. 10, 2017

(65) Prior Publication Data

US 2017/0199207 A1    Jul. 13, 2017

Related U.S. Application Data

(63) Continuation of application No. 13/825,379, filed as application No. PCT/US2011/052591 on Sep. 21, 2011, now abandoned.

(60) Provisional application No. 61/384,969, filed on Sep. 21, 2010.

(51) Int. Cl.
*G01N 33/53* (2006.01)
*G01N 33/92* (2006.01)
*G01N 33/68* (2006.01)
*A61K 31/122* (2006.01)
*A61K 45/06* (2006.01)
*A61K 9/00* (2006.01)

(52) U.S. Cl.
CPC ............ *G01N 33/92* (2013.01); *A61K 9/0053* (2013.01); *A61K 31/122* (2013.01); *A61K 45/06* (2013.01); *G01N 33/6887* (2013.01); *G01N 2800/324* (2013.01); *G01N 2800/56* (2013.01)

(58) Field of Classification Search
None
See application file for complete search history.

(56) References Cited

U.S. PATENT DOCUMENTS

2005/0148517 A1    7/2005  Lockwood et al.

OTHER PUBLICATIONS

Chew et al. Diabetes Care 2008 vol. 31, p. 1502-1509.
Luc et al. (Arterioscler Thrornb Vaso Biol. 2002 vol. 22, p. 1155-1161.
Rundek et al. (Arch Neurol. 2004 vol. 61, p. 889-892).
Folker et al. (PNAS 1985 vol. 82, p. 901-904).

*Primary Examiner* — Jacob Cheu
(74) *Attorney, Agent, or Firm* — Tarolli, Sundheim, Covell & Tummino LLP

(57) ABSTRACT

A method for predicting myocardial damage in a subject having or at risk of cardiac disease includes determining a level of apolipoprotein AI (ApoAI) and a level of Coenzyme $Q_{10}$ ($CoQ_{10}$) in the subject and comparing the determined levels of ApoAI and $CoQ_{10}$ to control levels.

21 Claims, 4 Drawing Sheets

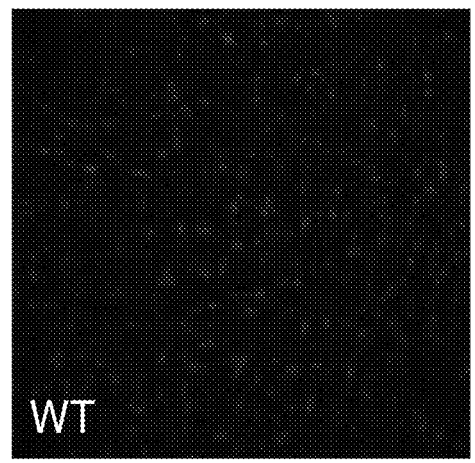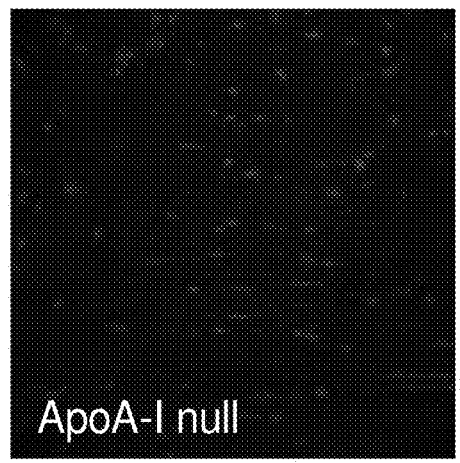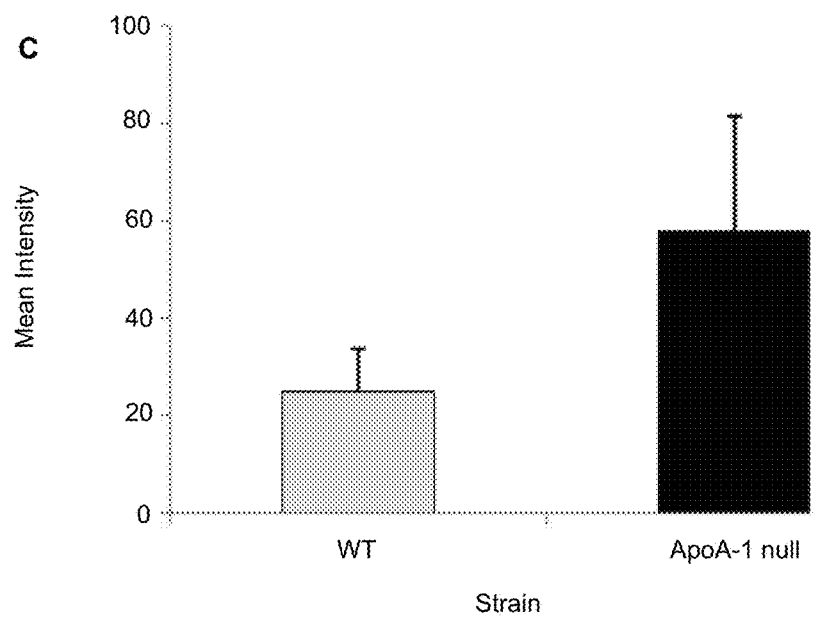
Fig. 2A
Fig. 2B
Fig. 2C

Individual Complexes

Pathway Flux

METHODS FOR PREDICTING AND TREATING MYOCARDIAL DAMAGE

CROSS-REFERENCE TO RELATED APPLICATIONS

This application is a continuation of U.S. application Ser. No. 13/825,379, filed Mar. 21, 2013; which is a 35 U.S.C. §371 national phase filing of International Application No. PCT/US2011/052591, filed Sep. 21, 2011, which claims which claims priority to U.S. Provisional Application 61/384,969, filed, Sep. 21, 2010. Each of the aforementioned applications is hereby incorporated by reference in its entirety.

TECHNICAL FIELD

This application relates generally to methods and kits for predicting myocardial damage in a subject having or at risk of cardiac disease and to methods for mitigating ischemic damage in a subject having an increased risk of myocardial damage resulting from cardiac.

BACKGROUND OF THE INVENTION

Plasma levels of high-density lipoproteins (HDL) and apolipoprotein AI (ApoAI) are inversely associated with cardiovascular morbidity and mortality. ApoAI is primarily synthesized in the liver and small intestine, and comprises a single polypeptide of 243 amino acid residues with a molecular weight of approximately 28,000 Da. ApoAI, through activation of lecithin:cholesterol acyltransferase, catalyzes the reaction of cholesterol and phosphatidylcholine to yield cholesterol esterified with a long-chain fatty acid and 2-lysophosphatidylcholine, an important step in reverse cholesterol transport.

The importance of HDL cholesterol as an independent risk factor for coronary artery disease (CAD) is well known. Novel therapeutic approaches for administering HDL protein, ApoAI, or ApoAI analogues to alter the development of atherosclerosis have been investigated in animal models and in humans. In fact, individuals with ApoAI deficiency and ApoAI-deficient mice fail to form normal HDL particles and, as a result, are predisposed to premature CAD.

Recent studies have also shown anti-inflammatory properties of ApoAI. For example, the inhibitory activity of ApoAI appears to be specifically directed to contact-mediated monocyte activation by T-cells through inhibition of TNF-α and IL1β. In addition to anti-inflammatory and anti-atherogenic function, reduced plasma concentrations of HDL and ApoAI have been implicated in the development of Type 2 diabetes.

SUMMARY OF THE INVENTION

An aspect of the application relates to a method for predicting myocardial damage in a subject having or at risk of cardiac disease. The method includes determining a level of apolipoprotein AI (ApoAI) and a level of $CoQ_{10}$ in the subject. The method further includes comparing the determined levels of ApoAI and a $CoQ_{10}$ to control levels. A decreased level of ApoAI and a decreased level of $CoQ_{10}$ compared to control levels are indicative of the subject having an increased risk of greater myocardial damage following a myocardial infarction.

Another aspect of the application relates to a method for determining increased risk of greater myocardial damage in a subject having or at risk of cardiac disease. The method includes determining a level of apolipoprotein AI (ApoAI) and a level of $CoQ_{10}$ in the subject. The method further includes comparing the determined levels of ApoAI and a $CoQ_{10}$ to control levels. A decreased level of ApoAI and a decreased level of $CoQ_{10}$ compared to control levels are indicative of the subject having an increased risk of greater myocardial damage following a myocardial infarction.

Another aspect of the application relates to a kit for predicting myocardial damage in a subject having or at risk of cardiac disease. The kit includes a first reagent for determining a level of ApoAI in the subject. The kit also includes a second reagent for determining a level of $CoQ_{10}$ in the subject and instructions for predicting myocardial damage in a subject having or at risk of cardiac disease.

A further aspect of the application relates to a method of mitigating ischemic damage in a subject having an increased risk of myocardial damage resulting from cardiac disease. The method includes administering therapeutically effective amounts of $CoQ_{10}$ and a hypolipidemic agent to a subject, which has decreased levels of ApoAI and $CoQ_{10}$ as compared to a control.

Yet another aspect of the application relates to a pharmaceutical composition for mitigating ischemic damage in a subject having an increased risk of myocardial damage resulting from cardiac disease. The pharmaceutical composition includes therapeutically effective amounts of $CoQ_{10}$ and a hypolipidemic agent.

BRIEF DESCRIPTION OF THE DRAWINGS

The foregoing and other features of the present invention will become apparent to those skilled in the art to which the present invention relates upon reading the following description with reference to the accompanying drawings, in which:

FIGS. 2A-B are a series of images following hydroethidine staining for reactive oxygen species (ROS) production in myocardial tissue from WT (FIG. 2A) and ApoAI-null (FIG. 2B) mice 1 hour after reperfusion. FIG. 2C illustrates the mean intensity quantified over 4 animals per group. Twelve random images from within the infarct zone from each animal were quantified (data represent mean±SD);

FIG. 3A is a plot comparing the relative activities of complex I, complex II, and complex III. FIG. 3B is a plot comparing the relative activity of NADH cytochrome c reductase (NCR) and succinate cytochrome c reductase (SCR)

DETAILED DESCRIPTION

Figure 1:
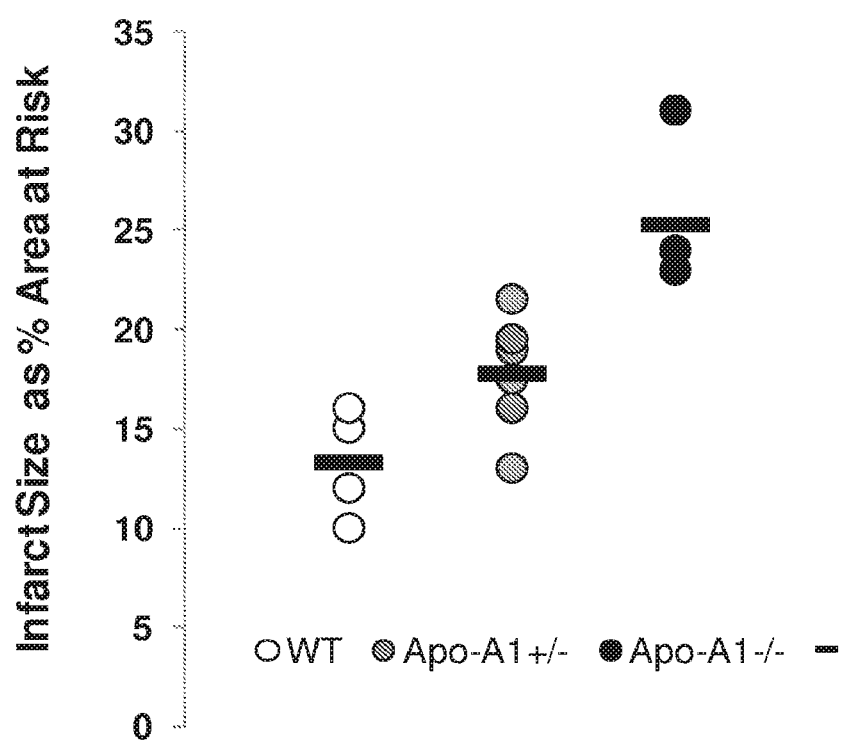
FIG. 1 is a plot comparing infarct size as a percent area at risk (AAR) in wild-type (WT), ApoAI-heterozygote (+/−), and ApoAI-null (−/−) mice after 30 minutes of ischemia and 3 hours of reperfusion (data represent mean+/−SD)

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., *Glossary of Genetics: Classical and Molecular*, 5th Ed., Springer-Verlag: New York, 1991, and Lewin, *Genes V*, Oxford University Press: New York, 1994. The definitions provided herein are to facilitate understanding of certain terms used frequently herein and are not meant to limit the scope of the present invention.

As used herein, the term "polypeptide" can refer to an oligopeptide, peptide, polypeptide, or protein sequence, or to a fragment, portion, or subunit of any of these, and to naturally occurring or synthetic molecules. The term "polypeptide" can also include amino acids joined to each other by peptide bonds or modified peptide bonds, i.e., peptide isosteres, and may contain any type of modified amino acids. The term "polypeptide" can also include peptides and polypeptide fragments, motifs and the like, glycosylated polypeptides, and all "mimetic" and "peptidomimetic" polypeptide forms.

As used herein, the term "amino acid" can refer to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. "Amino acid analogs" can refer to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" can refer to chemical compounds that have a structure that is different from the general chemical structure of an amino acid, but function in a manner similar to a naturally occurring amino acid.

As used herein, the term "polynucleotide" can refer to oligonucleotides, nucleotides, or to a fragment of any of these, to DNA or RNA (e.g., mRNA, rRNA, tRNA) of genomic or synthetic origin which may be single-stranded or double-stranded and may represent a sense or antisense strand, to peptide nucleic acids, or to any DNA-like or RNA-like material, natural or synthetic in origin, including, e.g., iRNA, ribonucleoproteins (e.g., iRNPs). The term can also encompass nucleic acids, i.e., oligonucleotides, containing known analogues of natural nucleotides. Additionally, the term can encompass nucleic acid-like structures with synthetic backbones.

As used herein, the term "pharmaceutically acceptable carrier" can include any material, which when combined with a conjugate retains the conjugate's activity and is non-reactive with a subject's immune system. Examples include, but are not limited to, any of the standard pharmaceutical carriers, such as a phosphate buffered saline solution, water, emulsions such as oil/water emulsion, and various types of wetting agents. Other carriers may also include sterile solutions, tablets including coated tablets, and capsules. Typically, such carriers contain excipients, such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

As used herein, the term "subject" can refer to any animal, including, but not limited to, humans and non-human animals (e.g., rodents, arthropods, insects, fish (e.g., zebrafish)), non-human primates, ovines, bovines, ruminants, lagomorphs, porcines, caprines, equines, canines, felines, aves, etc.), which is to be the recipient of a particular treatment. Typically, the terms "patient" and "subject" are used interchangeably herein in reference to a human subject.

As used herein, the terms "administer" or "administering" can refer to oral administration, administration as a suppository, topical contact, intravenous, intraperitoneal, intramuscular, intralesional, intranasal or subcutaneous administration, or the implantation of a slow-release device e.g., a mini-osmotic pump to a subject. Administration can be by any route, including parenteral and transmucosal (e.g., oral, nasal, vaginal, rectal or transdermal). Parenteral administration can include, e.g., intravenous, intramuscular, intra-arteriole, intradermal, subcutaneous, intraperitoneal, intraventricular, and intracranial. Other modes of delivery can include, but are not limited to, the use of liposomal formulations, intravenous infusion, transdermal patches, etc.

As used herein, the terms "cardiac disease," "cardiac disorder," "cardiovascular disease", "cardiovascular disorder," or "cardiovascular condition" can refer to any disease or disorder that negatively affects the cardiovascular system. The terms can also refer to cardiovascular events. "Cardiovascular events", as used herein, can include acute coronary syndrome, myocardial infarction, myocardial ischemia, chronic stable angina pectoris, unstable angina pectoris, angioplasty, stroke, transient ischemic attack, claudication(s) and vascular occlusion(s). Cardiac diseases and disorders, therefore, can include acute coronary syndrome, myocardial infarction, myocardial ischemia, chronic stable angina pectoris, unstable angina pectoris, angioplasty, stroke, transient ischemic attack, claudication(s), vascular occlusion(s), arteriosclerosis, left ventricular dysfunction, heart failure, and cardiac hypertrophy.

This application relates to methods for diagnosing, predicting, and/or determining an increased risk of myocardial damage in a subject and to methods for mitigating myocardial damage in a subject having an increased risk of myocardial damage resulting from cardiac disease. It was found that: (1) myocardial infarct (MI) size in apolipoprotein AI (ApoAI)-deficient mice is substantially greater than MI size in wild-type (WT) mice; (2) prophylactic treatment of ApoAI-deficient mice with Coenzyme $Q_{10}$ ($CoQ_{10}$) prior to MI leads to a 100% decrease in MI size; and (3) analyses of mitochondrial function in WT and ApoAI-deficient mice suggests that there is a defect in the mitochondria of ApoAI-deficient mice that leads to decreased flux in the succinate cytochrome c reductase (SCR) pathway secondary to a deficiency in the Q pool.

Based on these discoveries, it was determined that subjects, which have decreased ApoA1 and $CoQ_{10}$ levels compared to control subjects have increased myocardial damage (e.g., ischemic damage) following myocardial infarction and that the ApoA1 and $CoQ_{10}$ levels of a subject can be measured to determine or predict if the subject has increased risk of greater myocardial damage (e.g., ischemic damage) following myocardial infarction. The ability to determine a subject as having an increased risk of greater myocardial damage, therefore, provides a useful diagnostic tool to predict the amount of myocardial damage in a subject resulting from cardiac disease and to help mitigate or prevent myocardial damage in subjects at risk of cardiovascular disease (e.g., MI).

Accordingly, an aspect of the application relates a method for predicting myocardial damage in a subject having or at risk of cardiac disease. The method includes determining the levels of the cardiac markers, apolipoprotein and $CoQ_{10}$ in a subject.

As used herein, the term "apolipoprotein" can refer to apolipoproteins known to those of skill in the art and variants and fragments thereof. Apolipoproteins are proteins that bind to lipids and transport dietary fats through the bloodstream. Apolipoproteins that may be used as cardiac markers to predict the amount of myocardial damage in a subject include, but are not limited to, Apolipoprotein (Apo) A (e.g., ApoAI, ApoAII, ApoIV and ApoV), ApoB (e.g., ApoB48 and ApoB100), ApoC (e.g., ApoCI, ApoCII, ApoCIII and ApoCIV), ApoD, ApoE and Apo H. In one example, the level of ApoAI (e.g., an ApoAI polypeptide) in a subject can be used to determine an increased risk of greater myocardial damage in a subject.

ApoAI is the major protein component of high-density lipoprotein complex (HDL) and chylomicrons secreted from the intestinal enterocyte also contain ApoAI, however it is quickly transferred to HDL in a subject's bloodstream. Accordingly, the application also contemplates that a level of HDL in a subject can be indicative of a level of ApoAI in the subject. Therefore, in another example, the levels of HDL and $CoQ_{10}$ in a subject can be used to determine an increased risk of greater myocardial damage in a subject.

The levels of the cardiac markers (e.g., ApoAI and $CoQ_{10}$) can be determined by first obtaining one or more biological samples from a subject. In one example, the levels of the cardiac markers ApoAI and $CoQ_{10}$ can both be determined by first obtaining a single biological sample from a subject. In another example, the levels of the cardiac markers, ApoAI and $CoQ_{10}$, can each be determined separately by obtaining two or more biological samples from a subject.

The subject can be an apparently healthy subject, a subject at risk for a cardiovascular disease, or a subject known to have cardiovascular disease. "Apparently healthy", as used herein, can refer to subjects who have not previously been diagnosed as having any signs or symptoms indicating the presence of a cardiac disease, a history of a cardiac disease, or evidence of a cardiac disease. Apparently healthy subjects may not otherwise exhibit symptoms of a cardiac disease. In other words, such subjects, if examined by a medical professional, would be characterized as healthy and free of symptoms of a cardiac disease.

Subjects at risk for a cardiac disease can exhibit any one or combination of risk factors for cardiovascular disease including, but not limited to, elevated blood pressure, an abnormal response to a stress test, elevated levels of myeloperoxidase, C-reactive protein, low density lipoprotein, cholesterol, or atherosclerotic plaque burden. Techniques for assessing cardiovascular disease risk factors are known in the art and can include coronary angiography, coronary intravascular ultrasound, stress testing (with and without imaging), assessment of carotid intimal medial thickening, carotid ultrasound studies with or without implementation of techniques of virtual histology, coronary artery electron beam computer tomography, cardiac computerized tomography (CT) scan, CT angiography, cardiac magnetic resonance imaging, and magnetic resonance angiography.

The biological sample can include whole blood samples and samples of blood fractions, such as serum and plasma. The biological sample may be fresh blood, stored blood (e.g., in a blood bank), or a blood fraction. The biological sample may be a blood sample expressly obtained for the assay(s) described herein or, alternatively, a blood sample obtained for another purpose which can be sub-sampled. In one example, the biological sample can comprise whole blood. Whole blood may be obtained from the subject using standard clinical procedures. In another example, the biological sample can comprise plasma. Plasma may be obtained from whole blood samples by centrifugation of anti-coagulated blood. Such process provides a buffy coat of white cell components and a supernatant of the plasma. In yet another example, the biological sample can comprise serum. Serum may be obtained by centrifugation of whole blood samples that have been collected in tubes that are free of anti-coagulant. The blood may then be permitted to clot prior to centrifugation. The yellowish-reddish fluid obtained by centrifugation is the serum.

Biological samples can be pretreated as necessary by dilution in an appropriate buffer solution, heparinized, concentrated if desired, or fractionated by any number of methods including, but not limited to, ultracentrifugation, fractionation by fast performance liquid chromatography, precipitation with dextran sulfate, or other known methods. Any number of standard aqueous buffer solutions employing one or a combination of buffers, such as phosphate, Tris, or the like, at physiological pH can also be used.

In one example, a biological sample including $CoQ_{10}$ can include serum. In another example, a biological sample can be obtained from a subject where the level of $CoQ_{10}$ included in the sample reflects the $CoQ_{10}$ tissue level instead of the dietary intake of a subject. For example a biological sample can include cultured skin fibroblasts, muscle biopsies and blood mononuclear cells.

After obtaining the biological sample from the subject, the levels of the cardiac markers (e.g., ApoAI and CoQ10) are determined using any one or combination of known biochemical assays or techniques. Examples of biochemical assays or techniques that can be used to determine the level of an ApoAI polypeptide, HDL, and/or $CoQ_{10}$ can include, for example, antibody based assays, such as ELISA and Western blots, mass spectroscopy (MS) (e.g., LC/ESI/MS/MS), fluorometric assays and chromatography (e.g., HPLC, affinity column, etc.). It will be appreciated that biochemical assays or techniques may also be used to determine the level of a cardiac marker comprising a polynucleotide. For example, the level of an mRNA encoding an ApoAI polypeptide can be determined using Northern blot analysis. Alternatively, the presence or absence of the gene encoding an ApoAI polypeptide can be determined using PCR, for example.

In an embodiment of the application, the level of $CoQ_{10}$ can be determined using high-performance liquid chromatography (HPLC) with electrochemical detection as described by Tang et al., *Clinical Chemistry* 2001; 47(2) 256-265), which is incorporated herein by reference.

Once the levels of the cardiac markers have been determined, the levels of the cardiac markers are compared to control levels in order to determine an increased risk of greater myocardial damage in a subject following a myocardial infarction. For example, the level of an ApoAI polypeptide in a biological sample can be determined using ELISA and the level of $CoQ_{10}$ in a biological sample can be determined using HPLC and then both levels can be compared to control levels or values of ApoAI and $CoQ_{10}$, respectively. The control levels can be based upon the level of an ApoA1 polypeptide or $CoQ_{10}$ in a comparable biological sample (or samples) obtained from a control population (e.g., the general population) or a select population of subjects. For example, the select population may be comprised of apparently healthy subjects, subjects determined to have myocardial damage resulting from cardiac disease, subjects determined to have little or no myocardial damage resulting from cardiac disease or from subjects at risk for a cardiac disease.

The control levels can be related to the levels used to characterize the levels of the ApoAI polypeptide and $CoQ_{10}$ obtained from the subject. For example, if the level of the ApoAI polypeptide is an absolute value, such as the units of ApoAI polypeptides per nil of blood, the control level can also based upon the units of ApoAI polypeptides per ml of blood in subjects of the general population or a select population. Similarly, if the level of the ApoAI polypeptide and $CoQ_{10}$ is a representative value, such as an arbitrary unit obtained from an ELISA, the control level can also be based on the representative value.

The control levels can also take a variety of forms. For example, the control levels can be a single cut-off value, such as a median or mean. The control levels can be established based upon comparative groups, such as where the risk in one defined group is double the risk of another defined group. The control levels can also be divided equally (or unequally) into groups, such as a low-risk group, a medium-risk group, and a high-risk group, or into quadrants, the lowest quadrant being subjects with the lowest risk the highest quadrant being subjects with the highest risk.

Control levels of ApoAI polypeptides and $CoQ_{10}$ in biological samples, for example, can be obtained (e.g., mean levels, median levels, or "cut-off" levels) by assaying a large sample of subjects in the general population or a select population and then using a statistical model, such as the predictive value method for selecting a positivity criterion or receiver operator characteristic curve that defines optimum specificity (highest true negative rate) and sensitivity (highest true positive rate), as described in Knapp, R. G. and Miller, M. C. (1992): *Clinical Epidemiology and Biostatistics*, William and Wilkins, Harual Publishing Co. (Malvern, Pa.), which is incorporated herein by reference.

Depending upon the levels or values of the cardiac markers when compared to the control levels, a determination can be made as to the risk of greater myocardial damage in the subject following a myocardial infarction. In some embodiments, the myocardial damage can be defined as the ratio of ischemic or infracted myocardial area to total myocardial area and, as described below, can be expressed as a percentage. In an example of the method, a reduced or decreased level of an ApoAI polypeptide in combination with a reduced level of $CoQ_{10}$ as compared to control value levels may indicate an increased risk of developing a greater amount of myocardial damage. Thus, a subject with a reduced level of an ApoAI polypeptide and a reduced level of $CoQ_{10}$ may have an increased risk of developing a larger infarct area in the left ventricle (e.g., as a result of MI) as compared to a control subject. Alternatively, a normal or increased level of an ApoAI polypeptide and $CoQ_{10}$ as compared to a control value level may indicate little or no risk of a subject developing greater or increased myocardial damage following MI.

In another aspect of the application, a kit is provided for diagnosing an increased risk of myocardial damage resulting from cardiac disease in a subject. The kit includes at least one first reagent that specifically detects and/or determines the level of ApoAI, such as an ApoAI polypeptide, an ApoAI polypeptide fragment, a polynucleotide encoding an ApoAI polypeptide, or a polynucleotide encoding a fragment of an ApoAI polypeptide in a subject, at least one second reagent that specifically detects and/or determines the level of $CoQ_{10}$, in a subject and instructions for using the kit to determine an increased risk of greater myocardial damage in a subject following a myocardial infarction.

In an example of the application, a first reagent can detect expression levels of an ApoAI polypeptide or fragment thereof via an antibody that specifically binds to the ApoAI polypeptide or fragment thereof. In other example, the first reagent can comprises a nucleic acid probe complementary to a polynucleotide sequence coding for an ApoAI polypeptide or fragment thereof. For example, the nucleic acid probe may be a cDNA or an oligonucleotide immobilized on a substrate surface.

The instructions of the kit can include instructions required by a regulatory agency (e.g., the U.S. Food and Drug Administration) for use in in vitro diagnostic products. For example, the instructions can be applicable to one or more of an extraction buffer/reagent(s) and a related protocol, an amplification buffer/reagent(s) and a related protocol, a hybridization buffer/reagent(s) and a related protocol, an immunodetection buffer/reagent(s) and a related protocol, a labeling buffer/reagent(s) and a related protocol, and/or a control value or values (as described above).

This application also relates to a method for mitigating ischemic damage in a subject having an increased risk of a myocardial damage resulting from cardiac disease. The method includes administering therapeutically effective amounts of a ubiquinone in combination with a hypolipidemic agent to the subject. In one example, the subject is determined to have an increased risk of a myocardial damage resulting from cardiac disease as described herein.

Administration of a ubiquinone "in combination with" or "in conjunction with" a hypolipidemic agent includes parallel administration (administration of both the agents to the patient over a period-of time, such as administration on alternate days for one month) co-administration (in which the agents are administered at approximately the same time, e.g., within about a few minutes to a few hours of one another), and co-formulation (in which the agents are combined or compounded into a single dosage form suitable for oral or parenteral administration).

As used herein, the term "therapeutically effective amounts" can refer to the amount of a ubiquinone administered to a subject in combination with an amount of a hypolipidemic agent that results in lowering or eliminating the risk of ischemic damage in a subject found to have an increased risk of myocardial damage. A therapeutically effective amount can also refer to a prophylactically effective amount. As used herein, a "prophylactically effective amount" is an amount of a ubiquinone and a hypolipidemic agent that, when administered to a subject, will have the intended prophylactic effect, e.g., preventing or delaying the onset (or reoccurrence) of cardiac disease or symptoms, or reducing the likelihood of the onset (or reoccurrence) of cardiac disease or symptoms. The full prophylactic effect does not necessarily occur by administration of one dose and may occur only after administration of a series of doses. Thus, a prophylactically effective amount may be administered in one or more administrations.

The ubiquinone co-administered with a hypolipidemic agent to the subject can include one or series of quinones, which are widely distributed in animals, plants and microorganisms, a ubiquinone mimetic, a ubiquinone variant, or a ubiquinone fragment. In one example of the present invention the ubiquinone co-administered to a subject with a hypolipidemic agent is $CoQ_{10}$.

CoQ functions as an agent for carrying out oxidation and reduction within cells. Its primary site of function is in the terminal electron transport system where it acts as an electron or hydrogen carrier between the flavoproteins (which catalyze the oxidation of succinate and reduced pyridine nucleotides) and the cytochromes. This process is carried out in the mitochondria of cells of higher organisms. CoQ plays an important role as an antioxidant to neutralize potentially damaging free radicals created in part by the energy-generating process. For example, $CoQ_{10}$ has antioxidant and membrane stabilizing properties that serve to prevent cellular damage resulting from normal metabolic processes.

The term "hypolipidemic agents" as used herein refers to several classes of pharmaceuticals that are well known to increase ApoAI levels and/or HDL levels in vivo. In some embodiments, a hypolipidemic agent administered to the subject in combination with ubiquinone in accordance with the application can include ApoAI polypeptides, ApoAI mimetics, ApoAI analogs, cholesteryl ester transfer protein (CETP) inhibitors and statins.

"ApoAI polypeptides" as used herein refers to ApoAI peptide fragments and full length proteins. By "ApoAI mimetics" or "mimetics of ApoAI" or "known mimetics of ApoAI" as used in the specification and in the claims, it is meant mimetics of ApoA1 that can be identified or derived from any reference and that have ApoA1 behavior. These include mimetics of ApoAI identified in U.S. and foreign patents and publications. For example, an ApoA1 mimetic described herein can include any number of peptidomimetics of ApoA1 designed to beneficially influence the lipid parameters and/or cholesterol levels in the blood. Accordingly, an ApoA1 polypeptide mimetics contemplated herein may include modified polypeptides from the ApoA1 forms and variants including, for example, apolipoprotein A-I (Brewer et al., (1978)), apolipoprotein A-1 Milano (Weisgraber (1983) J. Biol. Chem. 258: 2508-2513), apolipoprotein A-1 Marburg, (Utermann et al., (1982) J. Biol. Chem. 257: 501-507), apolipoprotein A-1 Paris (Biclicki and Oda (2002) Biochemistry 41, 2089-2096), proapolipoprotein A-1, or any other mutant form of ApoA1 known in the art whether synthetically formed or naturally occurring.

An ApoAI mimetic can also include an ApoAI agonist which mimics the function of ApoAI in a subject. An example of an ApoAI agonist includes the recombinant ApoAI mutant protein referred to as the 'milano' mutant. The Milano mutant ApoA1 has an Arginine to Cysteine mutation at amino acid position 197 (R197C) in the pre-pro-ApoA1 protein amino acid sequence (corresponding to R173C in the mature ApoA1 amino acid sequence). The cysteine in the milano mutant leads to the formation of an ApoA1 dimer, held together by a disulfide bond, due to the additional cysteine residue.

Additional ApoA1 mimetics include ApoA1 oxidant resistant mimetics, such as those describe in U.S. Pat. Appl. No. 20090149390A1, which is incorporated herein by reference. For example, an ApoA1 mimetic for use in a method described herein can include, but is not limited to, an ApoA1 mimetic having an amino acid sequence that includes at least a portion of the amino acid sequence of ApoA1 or a mimetic of the ApoA1 where at least one tryptophan has been substituted with an oxidation resistant amino acid, (e.g., phenylalanine) in the amino acid sequence of the ApoA1 mimetic. An ApoA1 mimetic for use in the present invention can also include stabilized Apo A1 protein variants such as those described in U.S. Pat. Appl. No.: 20100222276A1, which is incorporated herein by reference.

As used herein, the term "statins" or "statin drug" can refer to any compound or agent capable of substantially inhibiting HMG Co-A reductase. Statins are a family of molecules sharing the capacity to competitively inhibit the hepatic enzyme 3-hydroxy-3-methylglutaryl coenzyme A (HMG-CoA) reductase. This enzyme catalyses the rate-limiting step in the L-mevalonate pathway for cholesterol synthesis. Consequently, statins block cholesterol synthesis. Statins that can be administered, or co-administered to a subject according to the invention include, Compactin, Atorvastatin, Pravastatin, Lovastatin, Mevinolin, Pravastatin, Fluvastatin, Mevastatin, Visastatin/Rosuvastatin Velostatin, Cerivastatin, Simvastatin, Synvinolin, Rivastatin (sodium 7-(4-fluorophenyl)-2,6-diisopropyl-5-methoxymethylpyridin-3-yl)-3,5-dihydroxy-6-heptanoate), and Itavastatin/Pitavastatin. In one example, statins are administered orally from about 1 mg/day to about 40 mg/day.

Additional hypolipidemic agents for use in the compositions and methods described herein include but are not limited to bile acid sequestrants (resins), ezetimibe, phytosterols, olistat, acipimox CETP inhibitors, squalene synthase inhibitors, AGI-1067 and mipomersin. Clinically, the choice of an agent will depend on the patient's cholesterol profile, cardiovascular risk, and the liver and kidney functions of the patient evaluated against the balancing of the risks and benefits of the hypolipdemic agent.

A hypolipidemic agent administered to a subject in combination with an ubiquinone (e.g., $CoQ_{10}$) in accordance with the application can also include an agent that increases HDL-cholesterol in a subject. For example, an agent that increases HDL-cholesterol in a subject can include niacin and/or fibrates. In one example, pharmacologic niacin (about 1- to about 3-gram/day) can be administered to a subject in combination with $CoQ_{10}$.

The therapeutically effective amounts of ubiquinone (e.g., $CoQ_{10}$) and/or a hypolipidemic agent can be administered in an isolated or concentrated form, or as a part of one or more pharmaceutical compositions and/or formulations. In one embodiment, a pharmaceutical composition can include ubiquinone and a hypolipidemic agent as the active ingredient and a pharmaceutically acceptable carrier or aqueous medium excipient suitable for administration and delivery in vivo. Combined therapeutics are also contemplated, and the same type of underlying pharmaceutical compositions may be employed for both single and combined medicaments. For example, a pharmaceutical composition described herein can include ubiquinone and a hypolipidemic agent described above as the active ingredients and a pharmaceutically acceptable excipient suitable for administration and delivery in vivo.

A pharmaceutical composition described herein can be administered by any appropriate route, such as percutaneous, parenteral, subcutaneous, intravenous, intraarticular, intrathecal, intramuscular, intraperitoneal, or intradermal injections, or by transdermal, buccal, oromucosal, ocular routes, or via inhalation. The dosage administered will be dependent upon the age, health, and weight of the subject, kind of concurrent treatment, if any, frequency of treatment, and the nature of the effect desired. In a subject with both a decreased level of an ApoAI polypeptide and a decreased level of $CoQ_{10}$, for example, a therapeutically effective amount of a pharmaceutical composition comprising $CoQ_{10}$ can be prophylactically administered to prevent or mitigate ischemic damage (e.g., as a result of MI).

In addition to one or more active ingredients (e.g., $CoQ_{10}$), pharmaceutical compositions can include pharmaceutically acceptable carriers comprising excipients and auxiliaries that facilitate processing of an active ingredients into pharmaceutical preparations. The pharmaceutical preparations of the present invention can be manufactured in a known manner by, for example, means of conventional mixing, granulating, dragee-making, dissolving, or lyophilizing processes. Thus, pharmaceutical preparations for oral use can be obtained by combining the active agents with solid excipients, optionally grinding the resulting mixture, and processing the mixture of granules after adding suitable auxiliaries, if desired or necessary, to obtain tablets or dragee cores.

Suitable excipients can include fillers, such as saccharides (e.g., lactose or sucrose, mannitol or sorbitol), cellulose preparations and/or calcium phosphates (e.g., tricalcium phosphate or calcium hydrogen phosphate), as well as binders, such as starch paste using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as the above-mentioned starches, as well as carboxymethyl-starch, cross-linked polyvinyl pyrrolidone, agar, or alginic acid or a salt thereof, such as sodium alginate. Auxiliaries are flow-regulating agents and lubricants, for example, silica, talc, stearic acid or salts thereof, such as magnesium stearate, or calcium stearate, and/or polyethylene glycol. Dragee cores can be provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions, and suitable organic solvents or solvent mixtures.

To produce coatings resistant to gastric juices, solutions of suitable cellulose preparations, such as acetylcellulose phthalate or hydroxypropylmethylcellulose phthalate can be used. Slow-release and prolonged-release formulations may be used with particular excipients, such as methacrylic acid-ethylacrylate copolymers, methacrylic acid-ethyl acrylate copolymers, methacrylic acid-methyl methacrylate copolymers, and methacrylic acid-methyl methylacrylate copolymers. Dye stuffs or pigments can be added to the tablets or dragee coatings, for example, for identification to characterize combinations of active compound doses.

Other pharmaceutical preparations that can be used orally include push-fit capsules made of gelatin, as well as soft, sealed capsules made of gelatin and a plasticizer, such as glycerol or sorbitol. The push-fit capsules can contain the active compounds in the form of granules that may be mixed with fillers, such as lactose, binders, such as starches, and/or lubricants, such as talc or magnesium stearate and, optionally, stabilizers. In soft capsules, one or more active ingredients (e.g., $CoQ_{10}$) can be dissolved or suspended in suitable liquids, such as fatty oils or liquid paraffin.

Examples of formulations for parenteral administration can include aqueous solutions of one or more active ingredients in water-soluble form, for example, water-soluble salts, and alkaline solutions. Examples of salts can include maleate, fumarate, succinate, S,S tartrate, or R,R tartrate. In addition, suspensions of one or more of the active ingredients as oily injection suspensions can be administered. Suitable lipophilic solvents or vehicles include fatty oils, for example, sesame oil, or synthetic fatty acid esters, for example, ethyl oleate or triglycerides or polyethylene glycol-400. Aqueous injection suspensions can contain substances that increase the viscosity of the suspension, sodium carboxymethyl cellulose, sorbitol, and/or dextran.

The therapeutically effective amounts of the ubiquinone (e.g., $CoQ_{10}$) and a hypolipidemic agent can be administered to a subject on a desired dosing schedule. For example, a therapeutically effective amount of a pharmaceutical composition comprising $CoQ_{10}$ can be administered about four times daily, about three times daily, about twice daily, about daily, about every other day, about three times weekly, about twice weekly, about weekly, about every two weeks, or less often (as desired). In one example, a therapeutically effective amount of a pharmaceutical composition includes 30-1,200 milligrams of $CoQ_{10}$ taken orally in divided doses. In another example $CoQ_{10}$ can be administered intravenously at a dose of around 5 mg/kg of body weight.

A therapeutically effective amount of the ubiquinone (e.g., $CoQ_{10}$) and/or a hypolipidemic agent can also be administered for a duration sufficient to provide a prophylactic effect. For example, a therapeutically effective amount of $CoQ_{10}$ can be administered daily for one year, for about six months, about a year, about two years, about five years, about 10 years, or indefinitely. It will be apparent to those of skill in the art that the dose, dosing schedule, and duration can be adjusted for the needs of a particular subject, taking into consideration the subject's age, weight, severity of disease, and other co-morbid conditions.

Toxicity and therapeutic efficacy of compositions comprising ubiquinone and/or a hypolipidemic agent for use in the invention can be determined using standard pharmaceutical procedures in cell culture or experimental animals for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50.

The following example is for the purpose of illustration only and is not intended to limit the scope of the claims, which are appended hereto.

Example 1

Materials and Methods
LAD Ligation/Reperfusion and Quantification of Area at Risk and Infarct Size All animal protocols were approved by the Animal Research Committee, and all animals were housed in the Association for Assessment and Accreditation of Laboratory Animal Care International-approved animal facility of the Cleveland Clinic. Anterior wall MI (AMI) was performed as recently described (Askari, A. T. et al., *J. Exp. Med.* 197:615-624, 2003). Briefly, AMI was induced in eight 20- to 25-g male littermate wild-type (C57BL/6J), ApoA1 heterozygote ($ApoA1^{+/-}$) or knockout ($ApoA1^{-/-}$) mice by ligation of the LAD 7-0 Prolene. Blanching and dysfunction of the anterior wall verified LAD ligation. After 30 minutes of LAD ligation, microsurgical scissors were used to cut the knot in the ligature at the level of the myocardium, and animals subsequently underwent reperfusion for 3 hours. Successful reperfusion was verified by return of red color to the tissue that was initially blanched at the time of LAD ligation, as well as gross evidence of some recovery of anterior wall motion. Animals were kept on ventilator for the entire 3 hours of reperfusion and subsequently analyzed for area at risk and infarct size using 1% solution of 2,3,5-triphenyltetrazolium chloride (TTC) at 37° C. Briefly, once the LAD was ligated again, Evan's blue dye (1 mg/mL) was infused to define the volume of myocardium not at risk.

After Evan's blue dye infusion, the heart was harvested and sectioned into 3 pieces defined as the base, mid, and apex. The sections were incubated in TTC solution for 15 minutes, rinsed, and then placed in formalin overnight.

Determination of Reactive Oxygen Species (ROS) Production In Vivo

ROS production was assessed using in vivo hydroethidine dye (Kondo, T. et al., *J. Neurosci.* 17:4180-4189, 1997; Murakami, K. et al., *J. Neurosci.* 18:205-213, 1998), as previously described (Manabe, Y. et al., *Ann. Neurol.* 55:668-675, 200(4). Hydroethidine, a cell-permeable oxidative fluorescent dye, is oxidized to ethidium by superoxide (Carter, W. O. et al., *J. Leukoc. Biol.* 55:253-258, 1994; Bindokas, V. P. et al., *J. Neurosci.* 16:1324-1336, 1996). Ethidium, which exhibits peak absorbance at 520 nm and an emission maximum at 600 nm, is trapped intracellularly by intercalating with DNA (Rothe, G. et al., *Methods Enzymol.* 233:539-548, 1994). The fluorescence signal attributable to ethidium reflects cumulative ROS production during the period between administration of hydroethidine and killing of the animal. Hydroethidine (10 mg/kg) was injected into the jugular vein of anesthetized and previously infracted animal as described above and allowed to circulate for 4 h. Mice were killed, and hearts were removed and paraffin-embedded. Serial sections (n=5) were cut and collected at 600 μm intervals, and viewed with a confocal microscope. The analysis of ROS production was performed in a blinded manner by a different investigator. Five randomly selected areas within the infarct zone were selected and analyzed. Fluorescence intensity was measured in five serial sections per animal. The sum of the fluorescence intensity for each region was divided by the total number of pixels analyzed and expressed as relative fluorescence units.

TUNEL Assay

Heart sections were used to perform TUNEL staining with the In Situ Cell Death Detection kit (Roche Applied Science) per the manufacturer's instructions. Hearts were collected after 30 minutes ischemia/3 h reperfusion for assessment of TUNEL. Heart sections were incubated with TUNEL staining (Roche) for cell death and co-staining was performed using DAPI and cells were visualized with a confocal microscope. TUNEL-positive-staining cells were counted at 40× magnification in 5 randomly selected areas within the infarct zone and expressed as positive cells per $mm^2$ and then compared between WT and ApoAI KO mice. At least 10 sections were analyzed throughout the entire longitudinal axis of the hearts (n=5 hearts per group).

Mitochondrial Techniques

Three mouse hearts were pooled for isolation of cardiac mitochondria. Hearts were finely minced, placed in Chappell-Perry (CP 1) buffer (in mM: 100 KCl, 50 Mops, $5MgSO_4$, 1 EGTA, 1 ATP), trypsin added (1 mg/g wet weight), and homogenized with a polytron tissue processor (Brinkmann Instruments, Westbury, N.Y.) for 2.5 s at a rheostat setting of 3.5. The polytron homogenate was incubated in homogenization tube for 10 minutes with stirring at 4° C. CP 2 buffer (CP 1 with 2% fatty-acid free BSA), was added in the homogenate right after the incubation to stop the trypsin digestion. Additional mixing and homogenization was performed using 2 strokes with the loose pestle and 2 strokes with the tight pestle. Then, the homogenate was centrifuges at 500×g for 10 minutes. The supernatant was saved for isolation of mitochondria and the pallet was washed twice (centrifuge at 3000×g) and then resuspended in KME (in mM: 100 KCl, 50 MOPS, and 0.5 EGTA). Mitochondrial protein concentration was measured by the Lowry method, using bovine serum albumin as a standard.

Oxygen consumption in mitochondria was measured using a Clark-type oxygen electrode at 30° C. Mitochondria were incubated in a solution including 80 mM KCl, 50 mM MOPS, 1 mM EGTA, 5 mM $KH_2PO_4$ and 1 mg defatted, dialyzed BSA/ml at pH 7.4. Glutamate (complex I substrate, 20 mM) plus malate (2 mM), succinate (complex II substrate, 20 mM) plus rotenone (7.5 mM), and N,N,N',N'-tetramethyl p-phenylenediamine (TMPD)-ascorbate (complex IV substrate, 10 mM) plus rotenone (7.5 mM), were used. State 3 (ADP-stimulated), state 4 (ADP-limited) respiration, respiratory control ratios, the ADP/O ratio, and dinitrophenol-uncoupled respiration were determined. Endogenous substrates were depleted by addition of 0.1 mM ADP before glutamate stimulated respiration.

The following enzyme activities were measured in detergent-solubilized mitochondria using previously described methods (Hoppel, C. L. et al., *J. Clin. Invest.* 80:71-77, 1987; Lesnefsky, E. J. et al., *Am. J. Physiol.* 273:H1544-H1554, 1997); NADH-cytochrome c reductase (NCR, rotenone sensitive); succinate cytochrome c reductase (SCR)-antimycin A sensitive; complex II, thennoyltrifluroacetone (TTFA), sensitive; complex III, antimycin A sensitive, and citrate synthase (CS).

Net $H_2O_2$ production from mitochondria was measured using the oxidation of fluorogenic indicator amplex red in the presence of horseradish peroxidase. Amplex red assay was obtained from Molecular Probes (Eugene, Oreg.). Glutamate and succinate were used as complex I and complex 11 substrates, and the concentration of substrates is the same as that used to measure oxidative phosphorylation (Chen, Q. et al., *J. Biol. Chem.* 278:36027-36031, 2003.

Statistical Analyses

All data are expressed as mean±SD. Statistical analysis was performed with use of SPSS software (version 10.0 for Windows, SPSS Inc). Comparisons between two groups were statistically evaluated by Student's t-test. A value of $P \leq 0.05$ was considered statistically significant.

Results

Effect of Genetic Background on Infarct Size in Mice

Due to increased mortality rate in ApoAI KO mice after chronic ligation of the proximal left anterior descending artery (LAD) (~80-90% within the first 24 hrs), acute myocardial infarction was achieved by inducing 30 min of LAD ischemia and subsequent reperfusion for 3 hours. Mice were kept on ventilator for the entire experiment. There were no differences in the area at risk following LAD ligation between WT, ApoA-I+/− and ApoA-I−/− mice following LAD ligation, 49.9±1.2%, 49.7±3.2% and 51.7±4.4%, respectively. Conversely the infarct size as a percent of the AAR (IS/% AAR) correlated with the level of ApoA-1 with the largest infarcts seen in the ApoA-I null mice compared to ApoA-I het and WT mice (25.3±7.8%, n=4 vs. 17.8±3.0%, n=6 and 13.1±2.8%, n=4, respectively, FIG. 1). WT vs. ApoA-I het p=0.042; WT vs. ApoA-I null, p=0.002).

In Situ Detection of ROS

We postulated that the increase in infarct size in the ApoAI KO mice could be due to the increased production of ROS since ROS plays a major pathogenic role in ischemic injury. We used hydroethidine technique to quantify ROS release in WT and APOAI null mice after reperfusion (Representative images are shown in FIGS. 2A-B). There was a trend for an increase in mean fluorescence intensity in ApoAI null mice compared to WT mice (87.9±47 and 54.6±17.9, respectively, p=0.23, FIG. 2C).

In Situ DNA Fragmentation by TUNEL Staining

To determine if there was increased apoptosis is responsible for the observed injury in ApoAI KO mice, the TUNEL method was employed to detect apoptotic nuclei in myocardial cells. Quantitatively, the number of TUNEL positive cells/mm$^2$ trended higher in the ApoAI null mice compared to WT mice (19.7±13.5 and 12.1±11.1, respectively, p=0.17); however, this increase was not statistically significant.

Mitochondrial Oxidative Phosphorylation

Mitochondrial oxidative metabolism was measured with glutamate, succinate and TMPD-ascorbate as substrates. Oxygen consumption under ADP-stimulated (state 3), ADP-limited (state 4) conditions are shown in Table 1.

TABLE 2

Enzyme activities

| Enzyme | ApoAI KO (n = 4) | WT (n = 5) |
| --- | --- | --- |
| Complex I | 865 ± 71 | 810 ± 59 |
| NCR | 5120 ± 506 | 5612 ± 488 |
| Complex III | 5654 ± 580 | 6413 ± 449 |
| SCR | 334 ± 28* | 764 ± 50 |
| Complex II | 759 ± 75 | 789 ± 57 |
| Citrate Synthase | 3809 ± 166 | 4036 ± 78 |

Values are mean ± SE.
*P < 0.0001 vs. corresponding WT.

Figure 3A:
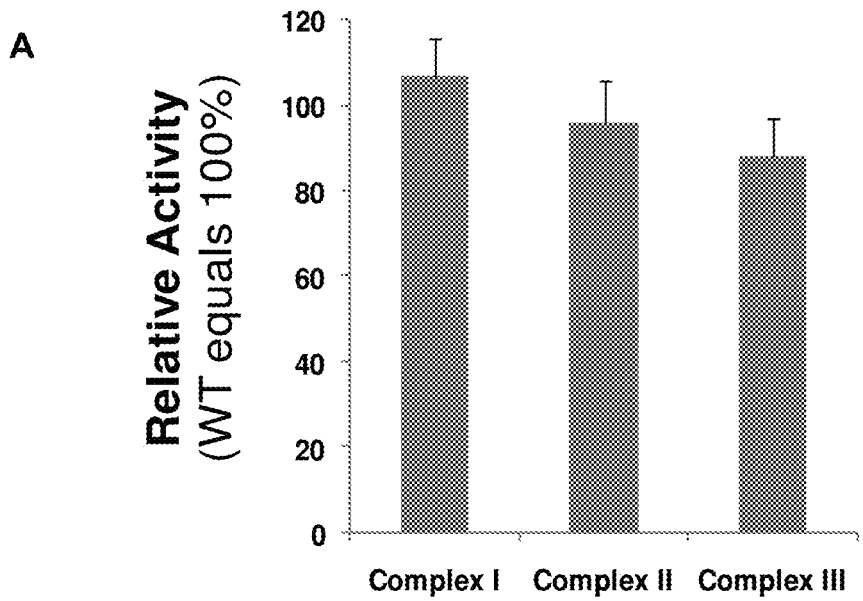
FIGS. 3A-B are a series charts showing electron transport chain activity.

However, the activity of complex III was not changed compared to WT mice and the activity of complex II was surprisingly normal (FIG. 3A). Thus, the defect in ETC of KO mice was likely at the Q pool, which altered the electron transfer from complex IT to complex III. The activity of

TABLE 1

Oxidative phosphorylation

| | ApoA1KO (n = 4) | | | | | WT (n = 5) | | | | |
| --- | --- | --- | --- | --- | --- | --- | --- | --- | --- | --- |
| Substrate | State 3 | State 4 | RCR | ADP/O | 2 mM ADP | State 3 | State 4 | RCR | ADP/O | 2 mM ADP |
| Glutamate | 288 ± 1.9 | 37 ± 3.4 | 8.3 ± 0.9 | 3.2 ± 0.1 | 345 ± 40 | 298 ± 17.9 | 38 ± 4 | 8 ± 0.4 | 3.3 ± 0.1 | 341 ± 44.7 |
| Pyruvate + Malate | 437 ± 16.2 | 59.6 ± 5.6 | 7.4 ± 0.5 | 3.6 ± 0.1 | 489.3 ± 32 | 416 ± 35.5 | 60 ± 14.7 | 7 ± 1 | 3.7 ± 0.3 | 454 ± 40.7 |
| Succinate | 575 ± 10* | 193 ± 10 | 3 ± 0*§ | 1.6 ± 0.1 | 555 ± 40 | 674 ± 29 | 193 ± 12 | 3.5 ± 0.1*§ | 1.6 ± 0.1 | 656 ± 28 |
| DHQ | 663 ± 30 | 217 ± 50 | 3.1 ± 0.5 | 1.6 ± 0.1 | 791 ± 48 | 570 ± 125 | 184 ± 19 | 3 ± 0.3 | 1.5 ± 0.1 | 648 ± 72 |
| TMPD | 1191 ± 65 | 1918 ± 134 | 206 ± 57 | 1712 ± 99 | | 1222 ± 52 | 1818 ± 70 | 246 ± 24 | 15.72 ± 55 | |

Values are means ± SE. Oxidative phosphorylation of glutamate in nanoatoms O min$^{-1}$ mg protein$^{-1}$.
RCR, respiratory control rate; ADP/O, ADP-to-O ratio.
*P < 0.05 vs. corresponding WT.
§P < 0.005.

State 3 respiration, state 4 respiration, respiration control ratio (RCR), and the ADP/O ratio were similar in WT and KO mice when glutamate was used as the substrate (Table 1). With succinate (plus rotenone), as a complex 11 substrate, a decrease in both state 3 respiration, and uncoupled respiration occurred in KO mice. The decreased coupling of respiration observed in KO mice indicated by the decrease in RCR was mainly due to a decreased state 3 respiration, rather than an increased state 4 respiration or phosphorylation apparatus defect since state 4 respiration was not altered in KO mice. Furthermore, dinitrophenol-uncoupled respiration was decreased in KO mice, localizing the respiratory defect to the electron transport chain (ETC).

Substrates that donate electrons to specific sites in the ETC were used under conditions of maximal ADP-stimulated respiration to identify sites of damage to the ETC. The maximal ADP-stimulated respiration measured using 2 mM ADP decreased in KO mice with succinate as substrate when respiration supported by electron flow from complex II, ubiquinone, complex III, cytochrome c and complex IV. In contrast, the maximal ADP-stimulated respiration was not affected in both WT and KO mice with glutamate, DHQ and TMPD-ascorbate as substrates when electron flow respectively from complex I, ubiquinone, complex III to final cytochrome c and complex IV.

ETC Enzyme Activities

Figure 3B:
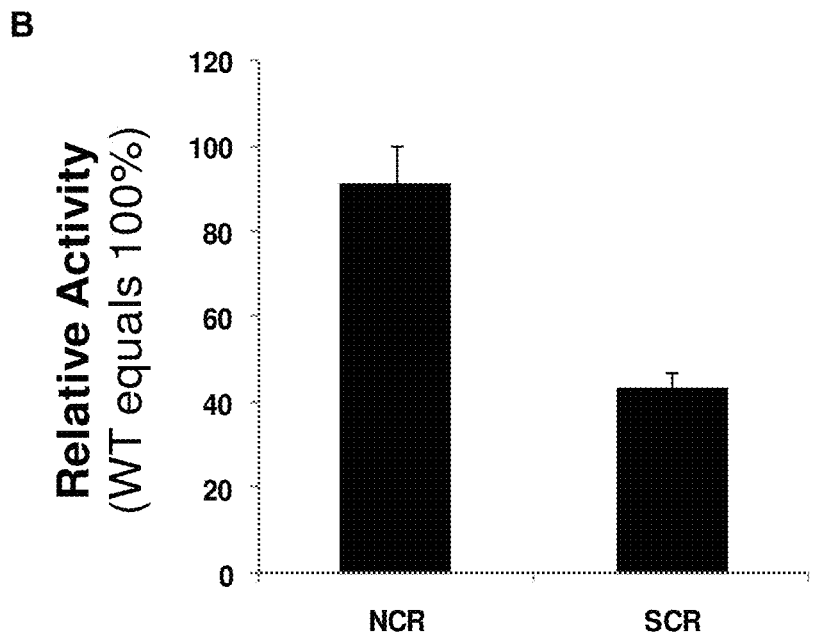

NADH cytochrome c reductase, measures of the activity of complex I and III was similar in both KO and WT mice (FIG. 3A). The activity of succinate cytochrome c reductase (SCR, antimycin A sensitive) was markedly decreased in KO mice, localizing a defect to complex II, ubiquinone and complex III of the ETC (Table 2).

citrate synthase, a mitochondrial matrix marker enzyme, was unaltered in both WT and KO mice (FIG. 3B).

$H_2O_2$ Production in Mitochondria

Since horseradish peroxidase and amplex red do not enter intact mitochondria, only $H_2O_2$ that is released from mitochondria (net release of $H_2O_2$, pmol/mg/30 min) is detected by this assay. The net production of $H_2O_2$ in WT and KO mice was similar with glutamate as complex I substrate, as well as with succinate plus rotenone as a complex II substrate (Table 3).

TABLE 3

Effect of genetic background of mice on mitochondrial $H_2O_2$ production

| | ApoAI KO (pmol/mg/30 min.) | WT (pmol/mg/30 min.) |
| --- | --- | --- |
| Complex I substrate | | |
| Glutamate/malate | 570 ± 73 | 872 ± 141 |
| Glutamate/malate plus rotenone | 271 ± 58 | 425 ± 66 |
| Complex II substrate | | |
| Succinate | 686 ± 117 | 923 ± 119 |
| Succinate plus rotenone | 207 ± 79 | 371 ± 8 |

Means ± SEM. Concentrations used: glutamate 10 mM, malate 2.5 mM, succinate 5 mM. When succinate was used as a substrate, rotenone (2.4 μm) was added.

Effect of CoQ10 on Infarct Size in ApoAI Null Mice

Figure 4:
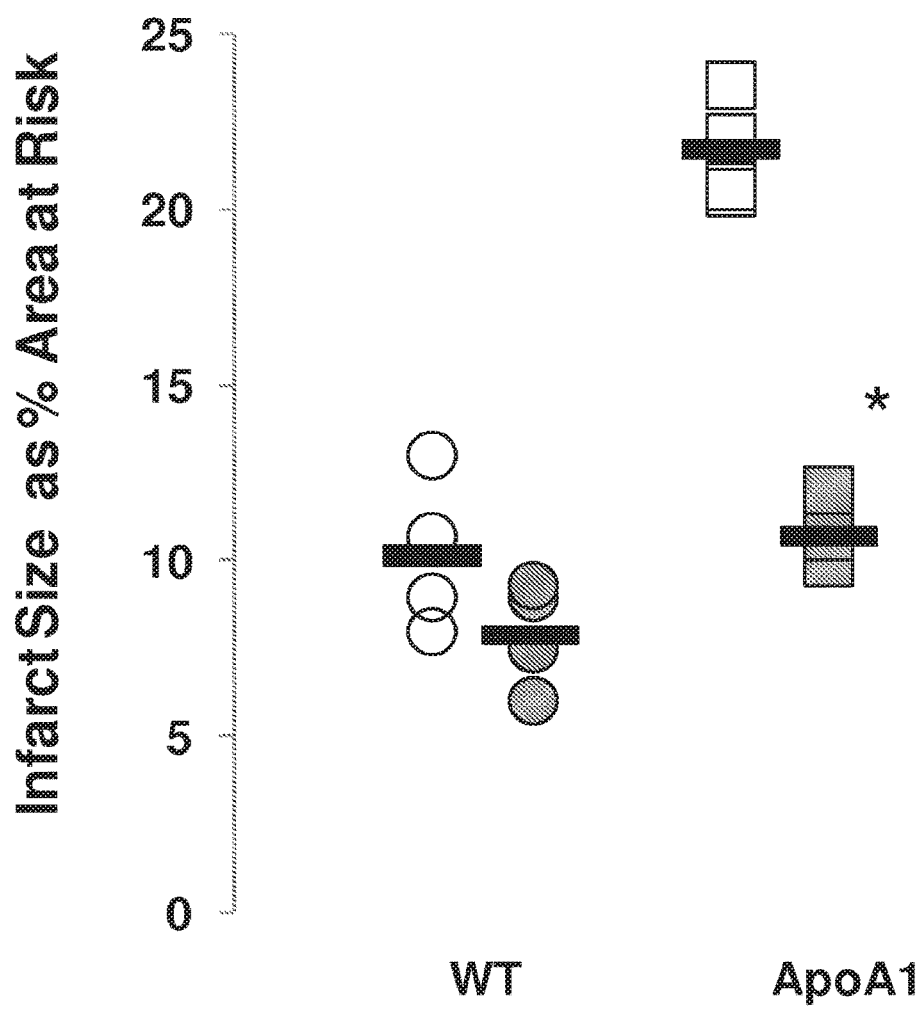
FIG. 4 is a plot comparing infarct size as a percentage of AAR in WT and ApoAI-null mice given saline or Coenzyme Q10 daily for 3 days prior to ischemia induced by 30 minutes of LAD ligation and 3 hours of reperfusion (data represent mean±SD; n=4-6 per group; *p<0.0001 compared to strain-matched NT control).

The analyses of mitochondrial function in the WT and ApoAI null mice suggested that there is a defect in the mitochondria of ApoAI null mice that leads to decreased flux in the succinate cytochrome c reductase pathway secondary to a deficiency in the Q pool. To determine if the Q pool was then a target for reversing the adverse effects of ApoAI deficiency, we inject CoQ10 ip (1 mg/kg/day) into WT and ApoAI null mice for 3 days prior to inducing ischemia reperfusion. The data in FIGS. 3A-B demonstrate that the administration of CoQ10 to ApoAI null mice completely corrected the defect seen in ApoAI null mice leading to >100% decrease in the infarct size as a percent area at risk (FIG. 4). There was a non-significant trend (p=0.15) towards a decrease in IS/% AAR in the WT mice treated with CoQ10 compared to WT controls.

From the above description of the invention, those skilled in the art will perceive improvements, changes and modifications. Such improvements, changes, and modifications are within the skill of the art and are intended to be covered by the appended claims.

Having described the invention, we claim:

1. A method for detecting susceptibility to myocardial damage in a subject having or at risk of cardiac disease, the method comprising:
   obtaining one or more bodily samples from the subject, the one or more bodily samples including $CoQ_{10}$ and ApoAI;
   determining a level of apolipoprotein AI (ApoAI) in the subject;
   determining a level of Coenzyme $Q_{10}$ ($CoQ_{10}$) in the subject;
   comparing the determined levels of ApoA1 and $CoQ_{10}$ to control levels, wherein a decreased level of ApoAI and a decreased level of $CoQ_{10}$ compared to control levels are indicative of the subject having an increased risk of greater myocardial damage following a myocardial infarction;
   administering therapeutically effective amounts of a ubiquinone in combination with a hypolipidemic agent to the subject having an increased risk of greater myocardial damage following a myocardial infarction.

2. The method of claim 1, the one or more bodily samples comprising plasma.

3. The method of claim 1, wherein the level of ApoAI in the subject is determined using an ELISA assay.

4. The method of claim 1, wherein the level of $CoQ_{10}$ in the subject is determined using high-performance liquid chromatography.

5. The method of claim 1, wherein the myocardial damage comprises a ratio of an area of ischemic myocardial tissue to total area of myocardial tissue.

6. The method of claim 1, the control levels include normal levels of ApoA1 and CoQ10 in a population of apparently healthy subjects.

7. The method of claim 1, wherein the cardiac disease is selected from the group consisting of myocardial infarction, coronary artery disease, angina, atherosclerosis, aneurysm, congestive heart failure, left ventricular dysfunction, cerebrovascular disease, and cerebrovascular accident.

8. A method of detecting an increased risk of greater myocardial damage in a subject having or at risk of cardiac disease, the method comprising:
   obtaining one or more bodily samples from the subject, the one or more bodily samples including $CoQ_{10}$ and ApoAI;
   determining a level of apolipoprotein AI (ApoAI) in the subject;
   determining a level of Coenzyme $Q_{10}$ ($CoQ_{10}$) in the subject;
   comparing the determined levels of ApoAI and $CoQ_{10}$ to control levels, wherein a decreased level of ApoAI and a decreased level of $CoQ_{10}$ compared to control levels are indicative of the subject having an increased risk of greater myocardial damage following a myocardial infarction;
   administering therapeutically effective amounts of a ubiquinone in combination with a hypolipidemic agent to the subject having an increased risk of greater myocardial damage following a myocardial infarction.

9. The method of claim 8, the one or more bodily samples comprising plasma.

10. The method of claim 8, wherein the level of ApoAI in the subject is determined using an ELISA assay.

11. The method of claim 8, wherein the level of $CoQ_{10}$ in the subject is determined using high-performance liquid chromatography.

12. The method of claim 8, wherein the myocardial damage comprises a ratio of an area of ischemic myocardial tissue to total area of myocardial tissue.

13. The method of claim 8, the control levels include normal levels of ApoA1 and CoQ10 in a population of apparently healthy subjects.

14. The method of claim 8, wherein the cardiac disease is selected from the group consisting of myocardial infarction, coronary artery disease, angina, atherosclerosis, aneurysm, congestive heart failure, left ventricular dysfunction, cerebrovascular disease, and cerebrovascular accident.

15. A method of determining increased risk of greater myocardial damage in a subject having or at risk of cardiac disease, the method comprising:
   obtaining one or more bodily samples from the subject, the one or more bodily samples including $CoQ_{10}$ and HDL;
   determining a level of HDL in the subject;
   determining a level of Coenzyme $Q_{10}$ ($CoQ_{10}$) in the subject;
   comparing the determined levels of HDL and $CoQ_{10}$ to control levels, wherein a decreased level of HDL and a decreased level of $CoQ_{10}$ compared to control levels are indicative of the subject having an increased risk of greater myocardial damage following a myocardial infarction;
   administering therapeutically effective amounts of a ubiquinone in combination with a hypolipidemic agent to the subject having an increased risk of greater myocardial damage following a myocardial infarction.

16. The method of claim 15, the one or more bodily samples comprising plasma.

17. The method of claim 15, wherein the level of HDL in the subject is determined using a fluorometric assay.

18. The method of claim 15, wherein the level of $CoQ_{10}$ in the subject is determined using high-performance liquid chromatography.

19. The method of claim 15, wherein the myocardial damage comprises a ratio of an area of ischemic myocardial tissue to total area of myocardial tissue.

20. The method of claim 15, the control levels include normal levels of HDL and CoQ10 in a population of apparently healthy subjects.

21. The method of claim 15, wherein the cardiac disease is selected from the group consisting of myocardial infarction, coronary artery disease, angina, atherosclerosis, aneurysm, congestive heart failure, left ventricular dysfunction, cerebrovascular disease, and cerebrovascular accident.

* * * * *